United States Patent [19]

Flax et al.

[11] Patent Number: 4,463,592

[45] Date of Patent: Aug. 7, 1984

[54] METHOD OF DETERMINING OPERATING CHARACTERISTICS OF ULTRASONIC SCANNING SYSTEMS

[75] Inventors: Stephen W. Flax; Gary H. Glover, both of Waukesha, Wis.

[73] Assignee: General Electric Company, Rancho Cordova, Calif.

[21] Appl. No.: 398,815

[22] Filed: Jul. 16, 1982

[51] Int. Cl.³ ............................................. G01N 29/00
[52] U.S. Cl. .................................................. 73/1 DV
[58] Field of Search ............. 73/1 DV, 631, 599, 627, 73/620, 602, 618; 128/660

[56] References Cited

U.S. PATENT DOCUMENTS

| | | | |
|---|---|---|---|
| 3,309,914 | 3/1967 | Weighart | 73/631 |
| 4,016,750 | 4/1977 | Green | 73/631 |
| 4,286,455 | 9/1981 | Ophir et al. | 73/1 DV |
| 4,361,043 | 11/1982 | Engle | 128/660 |

OTHER PUBLICATIONS

"Statistical Evaluation of the Doppler Ultrasonic Blood Flowmeter", Flax et al., ISA Transactions, vol. 10, #1, 1971.

Primary Examiner—Anthony V. Ciarlante
Attorney, Agent, or Firm—Flehr, Hohbach, Test, Albritton & Herbert

[57] ABSTRACT

The characteristics of an ultrasonic scanning system, including band-width, center frequency, and spectrum shape of reflected signals, are determined by directing ultrasonic energy from the system into a phantom having known ultrasonic attenuation and detecting the reflected ultrasonic signal for various depths in the phantom. Band-width is measured from the slope of frequency versus phantom depth. Center frequency is determined from the frequency of the signal reflected from the surface of the phantom. Spectrum shape is determined from the change in frequency of the reflected signal with change in phantom depth.

5 Claims, 2 Drawing Figures

METHOD OF DETERMINING OPERATING CHARACTERISTICS OF ULTRASONIC SCANNING SYSTEMS

This invention relates to ultrasonic scanning systems as used for medical diagnostic purposes, and more particularly the invention relates to determining the operating characteristics of such scanning systems.

Ultrasonic diagnostic systems are known and commercially available for medical diagnostic purposes. See for example U.S. Pat. No. 4,172,386 for "Video A Trace Display System for Ultrasonic Diagnostic System" and U.S. Pat. No. 4,204,433 for "Computerized Ultrasonic Scanner With Technique Select". The commercially available Datason ultrasound system of General Electric Company provides both real time and static images on a television display.

Briefly, such systems utilize sound transducers to transmit ultrasonic (e.g. on the order of several megahertz) waves into a patient and to receive reflected signals. The echo signals are applied to a time gain compensated amplifier to adjust the echo signals for attenuation in passing through the patient. The adjusted signals are then passed through an analog to digital conversion and video processing circuitry and thence to scan converter circuitry for display format.

Disclosed in co-pending patent application Ser. No. 06/369,423 filed Apr. 19, 1982 now U.S. Pat. No. 4,441,368 for Method and Means for Determining Ultrasonic Wave Attenuation in Tissue, is a method of determining frequency dependent attenuation at differing levels in tissue using a time domain analysis rather than a frequency domain analysis. More particularly, by counting the zero crossings of a reflected ultrasonic signal for different levels in tissue under examination and then comparing the zero crossing density at one level to the zero crossing density at a second level, the attenuation of the tissue between the two levels can be ascertained. The method and apparatus for determining zero crossing density is relatively simple and reliable.

The present invention is directed to characterizing the ultrasonic scanning system and particularly the frequency spectrum of reflected waves. Using a phantom tissue having known frequency attenuation, the nominal center frequency, bandwidth, and basic spectral shape of the reflected wave can be determined. The system can then be adjusted by altering components, as necessary, to enhance the diagnostic characteristics thereof.

Accordingly, an object of the invention is a method of characterizing an ultrasonic scanning system.

A feature of the invention is the use of a phantom having known frequency selective ultrasonic attenuation in characterizing an ultrasonic scanning system.

The invention and objects and features thereof will be more readily apparent from the following detailed description and appended claims when taken with the drawings, in which:

Figure 1:
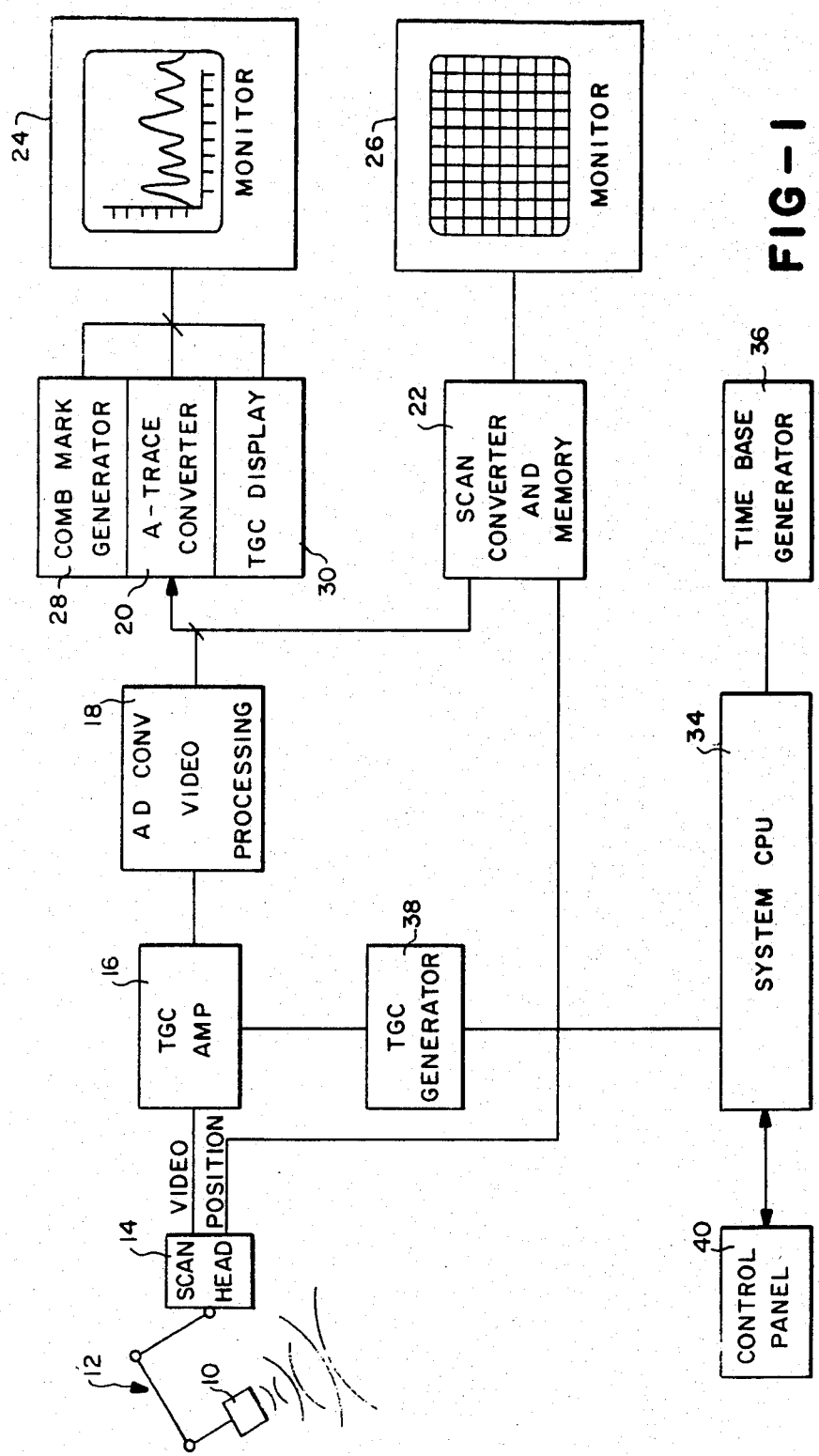
FIG. 1 is a functional block diagram of an ultrasonic scanning system.

Referring now to the drawings, FIG. 1 is a functional block diagram of an ultrasonic scanner. In this embodiment the system includes a transducer 10 mounted on a hinged arm system shown generally at 12 whereby transducer 10 can move freely in a single plane. Potentiometers in scanhead 14 and associated with the arms of the system generate signals indicative of the X and Y position of the scanner 10 in the plane of motion.

Transducer 10 transmits ultrasonic signals (e.g. on the order of 2 megahertz) and generates electrical signals in response to reflections of the transmitted ultrasonic signals. The generated signals are attenuated in time due to attenuation of the ultrasonic signal in passing through a patient.

The attenuated r.f. signal is then applied to a variable gain amplifier 16, and the amplified signal is then applied to analog to digital conversion and video processing circuitry 18. The output of circuitry 18 is then applied to A trace converter circuitry 20 and to scan converter and memory circuitry 22 which generate the signals for controlling television monitors 24 and 26, respectively.

The A trace converter generates a signal for real time display of the amplitude of each reflected ultrasonic wave. The A trace data applied to monitor 24 identifies a horizontal position on the monitor (e.g. 1,000 positions) and an amplitude or vertical position associated with each X position. This data controls the intensity of the electron beam in the display during raster line scanning by the beam. Scale markings for the displayed A trace are generated by comb mark generator 28, and a time gain compensation curve is provided by generator 30.

A section view of the patient is displayed on monitor 26 in response to the scan converter and memory 22. The signal from circuitry 18 is converted for storage in a 512×512 memory matrix with each point in the matrix accommodating a 5 bit brightness code. The matrix corresponds to the pixels on the display of monitor 26 with the brightness code being indicative of the Grayscale for the pixels. System control is provided by a central processing unit 34 which also controls a time base generator 36 which generates the timing signals for the system. A time gain compensation (TGC) control generator 38 generates the control signals for amplifier 16 and a control panel 40 is provided for manual control of the system through the central processing unit.

Figure 2:
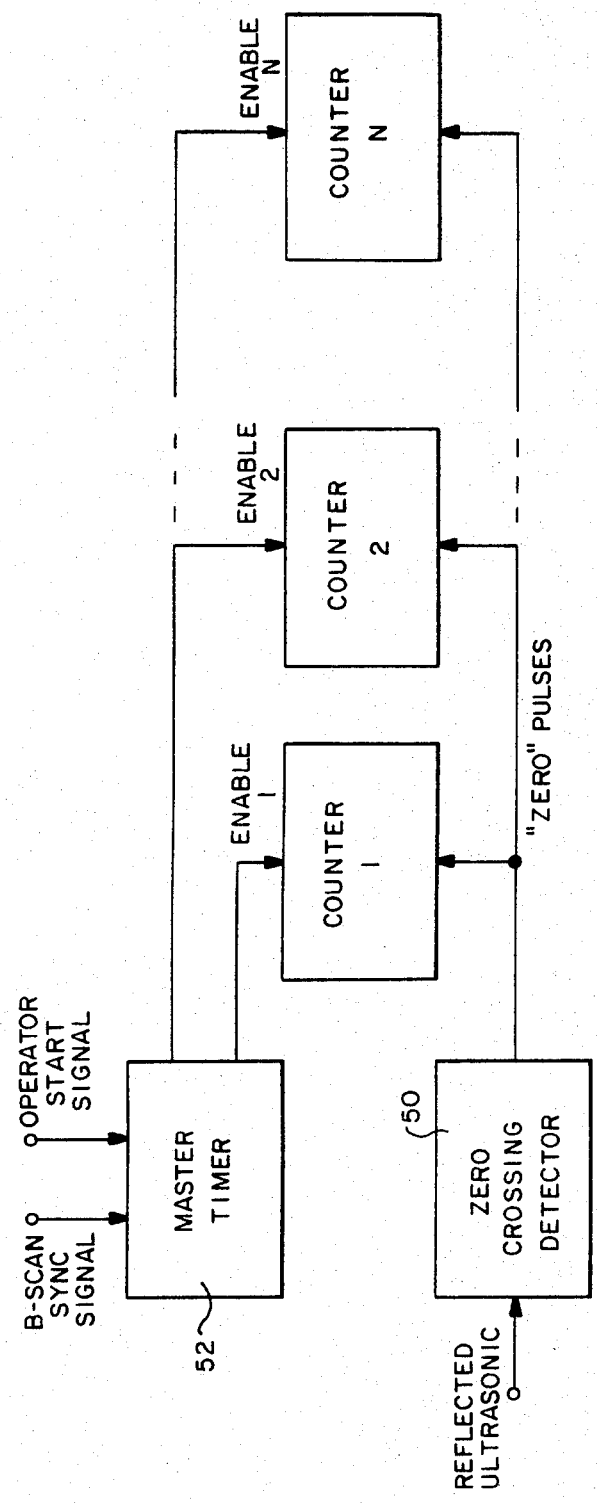
FIG. 2 is a functional block diagram of apparatus useful in establishing ultrasonic attenuation in tissue under analysis.

FIG. 2 is a functional block diagram of apparatus as disclosed in copending application Ser. No. 369,370, supra, in which a reflected ultrasonic signal from tissue under examination is applied to a zero crossing detector 50. The detector 50 preferably comprises a monostable multivibrator which is triggered by a Schmitt trigger whereby a pulse is generated in response to each zero crossing of the reflected signal. Such a Schmitt trigger and monostable multivibrator is commercially available, for example the Texas Instruments 74221 integrated circuit device. The output of the detector 10 is a series of pulses which are then connected to a plurality of counters such as counter 1, counter 2, – counter N. In a preferred embodiment each counter is a conventional pulse counter. Alternatively, each counter can comprise capacitive means for storing charge in response to the pulses.

A master timer 52 controls each of the counters whereby a count is accumulated for a specific interval of time corresponding to a depth in the tissue under examination. The master timer receives an operator start signal and a sync signal from the ultrasonic scanner, and enable signals are then generated for each of the counters based on the time of flight of an ultrasonic wave in the tissue under examination and the depth of the tissue from which zero crossings for reflected signals are to be counted.

By comparing the count at one level to the count at another level the frequency dependent attenuation of an acoustic wave therebetween is established. By so establishing the attenuation throughout the tissue under examination a more accurate time gain control signal is established for the time gain compensated amplifier in the ultrasonic scanning apparatus.

Because of the differing characteristics of ultrasonic scanning systems and components thereof, such as the transducer, the characterization of the scanning system is desirable prior to determining the attenuation throughout tissue under examination. Not only can a more accurate determination of attenuation be established, but also the scanning system can be altered as necessary to enhance the diagnostic characteristics thereof.

As described in copending application Ser. No. 369,370, supra, the measured zero crossing density, $\lambda$, is related to the frequency spectrum of the reflected ultrasonic signal as follows:

$$\lambda = 2 \left[ \frac{\int_0^\infty f^2 s(f) df}{\int_0^\infty s(f) df} \right]^{\frac{1}{2}}$$

Assuming that the spectrum s(f) is Gaussian in shape, then the resulting center frequency is given as $$f_{center\,freq} = f_o - \alpha_o l \sigma^2$$

where $f_o$ = nominal center frequency of the transducer
$\alpha_o$ = frequency selective attenuation (nepers/cm/mm)
$l$ = path length through tissue
$\sigma$ = transducer bandwidth
Thus $\lambda \approx 2[f_o - \alpha_o l \sigma^2]$ For characterizing tissues it is assumed that $\sigma^2$ is known, then the rate of change of $\lambda$ with depth is determined to give $\alpha_o$ i.e.

$$d\lambda/dl = 2\alpha_o \sigma^2$$

or $$\alpha_o = 1/2\sigma^2 \, d\lambda/dl$$

By using a phantom tissue having known ultrasonic attenuation, $\alpha_o$, the following three parameters can be determined:

1. Band-width:

$$\sigma = \left[ \frac{1}{2\alpha_o} \frac{d\lambda}{dl} \right]^{\frac{1}{2}}$$

i.e. the slope of $\lambda$ vs. l is a measurement of $\sigma$.
2. Center Frequency:
Since $\lambda = 2[f_o - \alpha_o l \sigma^2]$
if we count the zeros as the pulse just enters the phantom so that $l \approx 0$, we have $f_o \approx \lambda/2$. i.e. a measure of the nominal center frequency.
3. Spectrum Shape:
Since for a *Gaussian shaped spectrum*

$$\frac{d\lambda}{dl} = 2\alpha_o \sigma^2 = \text{constant},$$

The accuracy of the Gaussian approximation is tested by the variance in $d\lambda/dl$. Since it is generally accepted that the best pulse shape for imaging has a Gaussian shaped spectrum the adherence of $d\lambda/dl$ being straight is a measure of how nearly Gaussian the spectrum is.

By using the method of characterizing an ultrasonic system as described hereinabove, suitable adjustment can be made in using the ultrasonic scanning system in characterizing tissue under examination. Moreover, the method allows an operator to modify the system as needed to enhance the operating characteristics thereof.

While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

What is claimed is:

1. A method of characterizing frequency spectrum of an ultrasonic scanning system comprising the steps of
    directing ultrasonic energy from said system into a phantom having known ultrasonic attenuation,
    detecting the frequency of a reflected ultrasonic signal for various depths in said phantom,
    determining the slope of frequency versus depth as a measure of band-width of the reflected signal,
    determining center frequency of said system from the frequency of the reflected signal reflected from the surface of said phantom, and
    determining frequency spectrum shape from the change in frequency of the reflected signal with change in depth in said phantom.

2. The method as defined by claim 1 wherein the step of detecting frequency includes counting zero crossings of the reflected signal.

3. A method of characterizing bandwidth response of an ultrasonic scanning system comprising the steps of
    directing ultrasonic energy from said system into a phantom having known ultrasonic attenuation,
    detecting the frequency of a reflected ultrasonic signal for various depths in said phantom, and
    determining the slope of frequency versus depth as a measure of band-width of the reflected signal.

4. A method of determining center frequency of an ultrasonic scanning system comprising the steps of
    directing ultrasonic energy from said system into a phantom having known ultrasonic attenuation,
    detecting the frequency of a reflected ultrasonic signal for various depths in said phantom, and
    determining the center frequency of said system from the frequency of the reflected signal reflected from the surface of said phantom.

5. A method of characterizing an ultrasonic scanning system by frequency spectrum shape comprising the steps of
    directing ultrasonic energy from said system into a phantom having known ultrasonic attenuation,
    detecting the frequency of a reflected ultrasonic signal for various depths in said phantom, and
    determining frequency spectrum shape from the change in frequency of the reflected signal with change in depth in said phantom.

* * * * *

UNITED STATES PATENT AND TRADEMARK OFFICE
CERTIFICATE OF CORRECTION

PATENT NO. : 4,463,592

DATED : August 7, 1984

INVENTOR(S) : Stephen Flax, Gary Glover

It is certified that error appears in the above—identified patent and that said Letters Patent is hereby corrected as shown below:

The equation in Col. 3, line 25, should read as follows:

$$\lambda = 2 \left[ \frac{\int_0^\infty f^2 s(f) df}{\int_0^\infty s(f) df} \right]^{1/2}$$

Signed and Sealed this

Thirtieth Day of April 1985

[SEAL]

Attest:

DONALD J. QUIGG

Attesting Officer

Acting Commissioner of Patents and Trademarks